United States Patent [19]

Delfel et al.

[11] 4,152,214

[45] May 1, 1979

[54] PRODUCTION OF HOMODEOXYHARRINGTONINE AND OTHER CEPHALOTAXINE ESTERS BY TISSUE CULTURE

[75] Inventors: Norman E. Delfel; John A. Rothfus, both of Peoria, Ill.

[73] Assignee: The United States of America as represented by the Secretary of Agriculture, Washington, D.C.

[21] Appl. No.: 840,423

[22] Filed: Oct. 7, 1977

[51] Int. Cl.$^2$ .................................. C12D 13/00
[52] U.S. Cl. ........................................ 195/104
[58] Field of Search ............... 195/29, 104; 47/58, 47/DIG. 1

[56] References Cited

U.S. PATENT DOCUMENTS 3,628,287  12/1971  Staba et al. .................. 47/58

OTHER PUBLICATIONS

Powell et al, Journal of Pharmaceutical Sciences, vol. 61, No. 8, pp. 1227-1230; 1972.

Primary Examiner—Raymond N. Jones
Assistant Examiner—Robert J. Warden
Attorney, Agent, or Firm—M. Howard Silverstein; David G. McConnell; Curtis P. Ribando

[57] ABSTRACT

Tissue of *Cephalotaxus harringtonia* has been successfully cultured and cephalotaxine and its chemotherapeutically active alkaloid esters have been recovered from the resultant callus and the culture medium. A novel alkaloid compound, homodeoxyharringtonine, has also been discovered in the culture medium.

4 Claims, No Drawings

PRODUCTION OF HOMODEOXYHARRINGTONINE AND OTHER CEPHALOTAXINE ESTERS BY TISSUE CULTURE

BACKGROUND OF THE INVENTION

1. Field of the Invention

This invention relates to the production and recovery of alkaloid compounds known to be present in the tissues of the evergreen plant, *Cephalotaxus harringtonia*, and known to be active against lymphocytic leukemia in test mice. This invention also relates to the production of a novel alkaloid compound not previously identified in *C. harringtonia* plant material.

2. Description of the Prior Art

Among the alkaloids which have been isolated from *C. harringtonia* plant material are cephalotaxine and a number of its esters [Powell et al., Tetrahedron Lett. 4081 (1969); Powell et al., Tetrahedron Lett. 815 (1970); and Mikolajczak et al., Tetrahedron 28: 1995 (1972)]. Though cephalotaxine itself is inactive, some of its esters which are derived from relatively complex dicarboxylic moieties have been found to exhibit significant antitumor activity against lymphoid leukemia L1210 and P388 leukemia in mice [Powell et al., J. Pharm. Sci. 61(8): 1227–1230 (August 1972)]. Two of the esters, harringtonine and homoharringtonine, have been approved for preclinical evaluation at the National Cancer Institute. Continued biological testing of the active esters requires quantities which cannot be supplied by the relatively scarce natural sources.

Various active alkaloids have been produced synthetically. The preparation of deoxyharringtonine is taught by Mikolajczak et al. in U.S. Pat. No. 3,959,312 and natural (−) cephalotaxine has been esterified with a number of synthetic acids [Mikolajczak et al., J. Med. Chem. 20: 328 (1977)]. However, the yield and stereochemical purity from these synthetic techniques is not sufficiently high to provide a practical source of active esters.

SUMMARY OF THE INVENTION

We have now surprisingly discovered that dedifferentiated cells from *C. harringtonia* tissues can be successfully grown on artificial media and that the same chemotherapeutically active alkaloids are produced in culture as in the intact plant. Previous studies indicate that in many cases plants do not produce the same compounds in culture that they do as intact plants [Benjamin et al., Planta Medica 23: 394–397 (1973)]. This is especially true for the complex antitumor compounds previously investigated. Our method of alkaloid compound production comprises the steps of:

a. providing living tissue of *Cephalotaxus harringtonia*;
b. providing a nutrient culture medium suitable for callus formation from said tissue;
c. culturing said tissue on said medium to produce callus from said tissue; and d. recovering said alkaloid compounds from said callus and from said medium.

Finding the alkaloids in the medium was unexpected insofar as secondary metabolites are generally found only in the plant cell, or else in the medium only as a result of cell death. Of course, recovery of alkaloids from the culture medium rather than the callus tissue would be advantageous to commercial production. The discovery in the medium of a novel alkaloid compound, homodeoxyharringtonine, was also unexpected since it has not been previously reported in the intact plant.

It is therefore an object of this invention to grow dedifferentiated cells from *C. harringtonia* tissues in callus culture.

It is also an object of the invention to produce chemotherapeutically active alkaloid compounds by callus culture.

Another object of the invention is to recover alkaloids from the culture medium as well as from the callus tissue.

A further object of the invention is to produce a novel alkaloid compound.

Other objects and advantages of the invention will become readily apparent from the ensuing description.

DETAILED DESCRIPTION OF THE INVENTION

The plant material useful in this invention is obtained from the Japanese plumyew, *Cephalotaxus harringtonia*. Any plant variety of this species, such as *harringtonia* (Forbes) K. Koch, would produce the desired results. Tissue from any part of the plant, including the leaves, stems, and roots may be selected for inducing callus. However, for reasons of availability and growth rate, leaf tissue is normally preferred.

To prevent contamination of the culture, the tissue should be sterilized prior to introducing it to the culture medium. Any conventional sterilization technique, such as vacuum impregnation of a $HgCl_2$ solution, would normally be effective.

A suitable culture medium for both callus induction and subsequent growth is an aqueous solution of Murashige and Skoog's salt composition (Table I) supplemented with a variety of other nutrients as described in Table II.

Table I

| Inorganic Salt Compositions | | |
|---|---|---|
| Salt | Murashige and Skoog | White |
| $NH_4NO_3$ | 1650.0 | |
| $KNO_3$ | 1900.0 | 80.0 |
| $NaNO_3$ | | |
| $Ca(NO_3)_2 \cdot 4H_2O$ | | 300.0 |
| $CaCl_2 \cdot 2H_2O$ | 440.0 | |
| KCl | | 65.0 |
| $KH_2PO_4$ | 170.0 | |
| $NaH_2PO_4 \cdot H_2O$ | | 16.5 |
| $Na_2SO_4$ | | 200.0 |
| $MgSO_4 \cdot 7H_2O$ | 370.0 | 720.0 |
| $MnSO_4 \cdot 4H_2O$ | 22.3 | 7.0 |
| $Fe_2(SO_4)_3$ | | 2.5 |
| $FeEl_3 \cdot 6H_2O$ | | |
| $FeSO_4 \cdot 7H_2O$ | 27.8 | |
| $Na_2 \cdot EDTA$ | 37.3 | |
| $ZnSO_4 \cdot 7H_2O$ | 8.6 | 3.0 |
| $H_3BO_3$ | 6.2 | 1.5 |
| KI | 0.83 | 0.75 |
| $CuSO_4 \cdot 5H_2O$ | 0.025 | |
| $Na_2MoO_4 \cdot 2H_2O$ | 0.25 | |
| $CoCl_2 \cdot 6H_2O$ | 0.025 | |
| $AlCl_3$ | | |
| $NiCl_2 \cdot 6H_2O$ | | |

Table II

| Nutrient | Amount/liter |
|---|---|
| sucrose | 30 g. |
| protein hydrolyzate | 1 g. |
| inositol | 100 mg. |
| hypoxanthine | 25 mg. |
| thiamine | 0.1 mg. |
| riboflavin | 0.5 mg. |

Table II-continued

| Nutrient | Amount/liter |
| --- | --- |
| niacin | 0.5 mg. |
| kinetin | 1 mg. |
| naphthalene acetic acid | 10 mg. |

It is understood that modifications may be made in this medium such as substitution of other conventional salt compositions (e.g., White's), addition or deletion of various components, or alteration of proportions. For example, we have found that elimination of the ammonium nitrate and protein hydrolyzate did not alter the callus growth rate. Likewise, reduction of the sucrose content by half reduced the growth rate over a 3-month period by only about 20%. We also observed that once a callus is established, the requirements for some nutrients are functions of their availability. For example, elimination by depletion of vitamins, inositol, hypoxanthine, and the growth hormones does not appear to inhibit callus growth. Thus, it is apparent from these observations that determination of suitable and optimum media for induction and growth of callus would be within the skill of a person in the art.

The medium may be gelled with agar, preferably in an amount of 0.8-1.0%, though other amounts such as within the range of 0.1-5% could also be used depending upon the desired consistency. However, the agar tends to interfere with the isolation of the alkaloids from the medium subsequent to culturing. We therefore prefer an alternate embodiment in which a bridge constructed of filter paper or other absorbent material is at least partially immersed in the aqueous medium and transports the medium to the cultured tissue supported on the top.

Temperatures in the range of about 10°-40° C. and preferably in the range of about 20°-30° C. are suitable for inducing and growing callus from the plant tissue. Exposure to light is not necessary. Generally, callus induction requires between 7 and 21 days. Under the above-described conditions, the callus has a doubling time of approximately 30 days and continues to grow steadily for 3 to 4 months after which the growth rate begins to decline. Callus growth and alkaloid production can be revitalized by subculturing, in which the callus is divided and transferred to fresh media.

The chemotherapeutically active alkaloid compounds produced by the callus culture are essentially the same as those found in the intact plant including harringtonine, isoharringtonine, homoharringtonine, and deoxyharringtonine. Significant quantities of cephalotaxine and other alkaloids, such as homerythrina alkaloids, are also produced. The structural formulas of cephalotaxine and its active esters, as well as data related to administration to mice and activity against lymphoid leukemia L1210 and P388, are given in Powell et al., J. Pharm. Sci. 61(8): 1227-1230 (August 1972), which is herein incorporated by reference.

The callus culture of this invention additionally yields a novel alkaloid compound not heretofore identified in the intact plant. This compound has been named homodeoxyharringtonine and is represented by the following structural formula0

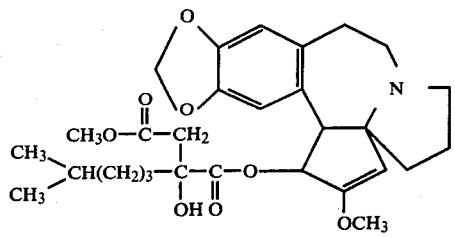

(Structures as drawn in this specification are not intended to indicate the stereochemistry of the compounds they represent and should not limit any compound herein to a specific structural configuration.) The chemotherapeutic activity of homodeoxyharringtonine can be readily predicted from its structural similarity to both homoharringtonine and deoxyharringtonine.

Cephalotaxine and its esters are found in both the callus and in the medium except for deoxyharringtonine and homodeoxyharringtonine which are unexpectedly found only in the medium. Another surprising discovery is that after 6 months, the level of all the alkaloids is greater in the medium than in the callus (Table II). Computations show that this phenomenon cannot be explained solely by concentration of the medium and therefore must represent active secretion by the callus. Recovery of the secreted alkaloids from the medium without the need for extraction from the callus tissue would of course be highly beneficial to commercial production.

Recovery of the alkaloids from the callus and medium may be by any conventional procedure as known in the art. For example, the extraction and purification procedures of Powell et al., Ind. Eng. Chem., Prod. Res. Dev. 13: 129 (1974), herein incorporated by reference, have proven to be effective.

As stated above, many plants are known to produce alkaloids in tissue culture, but quite often the compounds produced are not typical of the parent plant. While not desiring to be bound to any particular theory of operation, the surprising similarity of alkaloid distribution between the mature intact plants and the callus tissues of this invention may be due to slow tissue growth that would tend to favor secondary metabolism.

The following examples are intended only to further illustrate the invention and are not intended to limit the scope of the invention which is defined by the claims.

EXAMPLE 1

A young field-grown *C. harringtonia* tree approximately 30-cm. tall was planted in 2:1 peat moss:sandy loam in a 17-cm. diameter clay pot and grown under fluorescent light (1500 lx.) for a 16-hour day at 25°±3°. Shortly after planting, several branches were removed for callus initiation. These were sterilized alternately under vacuum and at atmospheric pressure to remove entrapped air from the leaves for 15 min. in a 0.1 HgCl$_2$ solution containing 1 drop detergent per 250 ml., rinsed twice in distilled water, and cut into 5-mm. pieces. Callus formation was induced by placing the stem and leaf pieces of the branches into 2-oz. wide-mouth bottles, having "Bakelite" caps with the cap liner removed, and containing 30 to 40 ml. of medium gelled with 0.8 to 1.0% agar. This and all subsequent operations were conducted using standard sterile technique and glassware and reagents which were autoclaved 30 min. at 120° C. The nutrient medium used for callus initiation was Murashige and Skoog's salt mixture (Table I) combined with the nutrients of Table II. About 50% of the samples were contaminated with fungi, Dothiorella spp. and Chaetomium spp., which were apparently growing inside the field-grown plant tissue and protected from the $HgCl_2$ sterilant. When the weight of the new callus from the uncontaminated samples reached approximately 0.5 g., wet basis, it was transferred to 30 to 40 ml. of fresh medium, removing at this time the remaining tissue of origin. The callus tissue was propagated for 13 months with subculturing by the above procedure approximately every 3 months.

EXAMPLE 2

Example 1 was repeated except that the plant tissue used to initiate the callus was new growth generated by the *C. harringtonia* tree under laboratory conditions. The contamination level of the resulting samples was less than 1%.

EXAMPLE 3

Example 2 was repeated except that White's salt mixture (Table I) was substituted for that of Murashige and Skoog. The resultant calluses were characterized by a growth rate slower than that of the samples of Example 2.

EXAMPLE 4

Eighty samples, each 0.5 g., wet basis, of callus grown by the procedure of Example 2 were placed in 2-oz. bottles on filter paper bridges made of Whatman No. 1 filter paper 9 cm. in diameter with 30 ml. of the following medium:

| Nutrient | Amount/liter |
| --- | --- |
| Murashige and Skoog's inorganic salt mixture (Table I) | |
| sucrose | 30 g. |
| protein hydrolyzate | 1 g. |
| thiamine | 0.1 mg. |
| riboflavin | 0.5 mg. |
| niacin | 0.5 mg. |
| naphthalene acetic acid | 10 mg. |
| kinetin | 1 mg. |

The bottles were divided into five replicate lots of 16 samples each. In addition to the above nutrients, 100 mg. inositol, 25 mg. hypoxanthine, 29 mg. orotic acid, and 1 mg. ascorbic acid were each independently added to half of the bottles of each lot according to the standard factorial statistical design for four factors at two levels (i.e., with or without the experimental additive). The tissues were transferred to fresh medium three times at 3-month intervals and harvested 2½ months thereafter. The entire experiment was duplicated. The dry weight (g./bottle) results showed none of the additives to be significantly favorable to tissue growth:

| | Av. g. of callus grown | |
| --- | --- | --- |
| | With | Without |
| inositol | 0.211 | 0.196 |
| hypoxanthine | 0.202 | 0.205 |
| orotic acid | 0.196 | 0.211 |
| ascrobic acid | 0.182 | 0.225 |

EXAMPLE 5

A statistically designed factorial experiment similar to that of Example 4 was conducted with five factors at two levels. The basal medium was:

| Nutrient | Amount/liter |
| --- | --- |
| $KNO_3$ | 1.9 g. |
| $CaCl_2$ | 332 mg. |
| inositol | 100 mg. |
| thiamine | 0.1 mg. |
| riboflavin | 0.5 mg. |
| niacin | 0.5 mg. |
| naphthalene acetic acid | 10 mg. |

One hundred twenty-eight bottles were divided into four replicate lots of 32 samples each. The above media of each lot was used with or without 1.65 g./l. $NH_4NO_3$, with or without 1 g./l. protein hydrolyzate, with 20 g./l. or 40 g./l. sucrose, with 1 mg./l. or 4 mg./l. kinetin, and with certain nutrients of Murashige and Skoog's sale mixture (Mg, $KH_2PO_4$, Fe, $Na_2$ EDTA, Mn, Zn, B, I, Mo, Cu, and Co) at ¼ or full strength. The four replicate bottles of each treatment were pooled, and the average dry weight was determined. The entire experiment was run in triplicate. The dry weight values (g. callus/bottle) were as follows:

| | Av. g. of callus (dry weight) | |
| --- | --- | --- |
| | With or higher level | Without or lower level |
| ammonium nitrate | 0.147 | 0.147 |
| protein hydrolyzate | 0.146 | 0.147 |
| sucrose | 0.164 | 0.130 |
| kinetin | 0.127 | 0.167 |
| minor nutrients (inorg. salts) | 0.163 | 0.131 |

The higher sucrose and nutrient salt level and the lower kinetin level were significantly better for *C. harringtonia* callus growth. In addition the amount of dry weight callus resulting from the two-way interaction between ammonium nitrate and protein was statistically significant:

| | Ammonium nitrate | |
| --- | --- | --- |
| | With | Without |
| protein hydrolyzate, with: | 0.136 g. | 0.157 g. |
| without: | 0.158 g. | 0.136 g. |

This indicates that either ammonium nitrate or protein hydrolyzate should be added but not both. The best combination of medium components in this experiment (i.e., 1.65 g. $NH_4NO_3$, no protein hydrolyzate, 40 g. sucrose, 1 mg. kinetin per liter plus full-strength nutrient salts) gave 0.282 g./bottle of dry callus.

EXAMPLE 6

Twenty-five milliliters of medium composed of Murashige and Skoog's salt mixture (Table I) and the nutrients of Table II but without the hypoxanthine were added to each of 30 bottles. Each bottle received a filter paper bridge made of Whatman No. 1 filter paper 9 cm. in diameter to support the 0.5 g. fresh weight of callus tissue. The bottles were divided at random into three groups of 10 each, placed into boxes, and covered with black plastic to exclude light (to ensure uniform conditions with respect to light). Each group was maintained at a different temperature; namely, 15°, 25°, and 35° C., respectively, for 3 months. The results below show a temperature near 25° C. to be optimum for callus growth.

| Temp. (° C.) | Dry weight of callus (g./bottle) |
|---|---|
| 15 | 0.14 |
| 25 | 0.25 |
| 35 | 0.13 |

EXAMPLES 7-8

Media were prepared comprising the Murashige and Skoog salt mixture (Table I) plus the following nutrients:

| Nutrient | Amount/liter | |
| | Example 7 | Example 8 |
|---|---|---|
| sucrose | 30 g. | 30 g. |
| protein hydrolyzate | 1 g. | 1 g. |
| inositol | 100 mg. | 100 mg. |
| hypoxanthine | 25 mg. | 25 mg. |
| thiamine | 0.1 mg. | 0.1 mg. |
| riboflavin | 0.5 mg. | 0.5 mg. |
| niacin | 0.5 mg. | 0.5 mg. |
| kinetin 1 mg. | 1 mg. | |
| naphthalene acetic acid | 10 mg. | 10 mg. |
| choline chloride | 10 mg. | — |
| ascorbic acid | 1 mg. | — |
| vitamin $B_6$ | 0.5 mg. | 1 mg. |
| vitamin $B_{12}$ | 0.5 μg. | 1 μg. |
| biotin | 10 μg. | 20 μg. |
| folic acid | 1 mg. | 2 mg. |
| pantothenic acid | 1 mg. | 2 mg. |

The media were gelled with 0.8-1.0% agar and callus tissue was grown thereon at 25° C. Both the callus and the spent medium were analyzed for alkaloid content at 3 months for Example 7 and at 3 and 6 months for Example 8.

In preparation for analysis, the callus tissue was dried to constant weight in a forced-air oven at 80°. The dried callus samples of from 3 to 10 g. were then pulverized with a mortar and pestle. Extraction and partial purification of the alkaloids was according to the procedure of Powell et al., supra, except for the omission of the countercurrent distribution step. The spent medium was analyzed similarly. To minimize emulsion problems, this medium was first diluted with an equal volume of $H_2O$, then adjusted to pH 9 and extracted three times with $CHCl_3$. Centrifugation facilitated phase separation. The combined $CHCl_3$ extracts were then extracted three times with 2% citric acid, and the citric acid solution was further purified according to the original method. Individual alkaloids were identified and quantitated by GC-MS method of Spencer et al., J. Chromatogr. 120: 335 (1976), herein incorporated by reference, using 3% OV-101 in addition to their Dexsil 300 liquid phase. All alkaloid values given below are based on the dry weight of the callus tissue.

Example 7 (3 months)

| Alkaloid | In callus (μg./kg.) | In medium (μg./kg.) | Total (μg./kg.) |
|---|---|---|---|
| cephalotaxine | 4,400 | 7,850 | 12,250 |
| deoxyharringtonine | 0 | 6,220 | 6,220 |
| homodeoxyharringtonine | 0 | 1,080 | 1,080 |
| isoharringtonine | 900 | 980 | 1,880 |
| harringtonine | 0 | 160 | 160 |
| homoharringtonine | 0 | trace | trace |

Example 8 (3 months)

| Alkaloid | In callus (μg./kg.) | In medium (μg./kg.) | Total (μg./kg.) |
|---|---|---|---|
| cephalotaxine | 1,070 | 2,770 | 3,840 |
| deoxyharringtonine | 0 | 3,880 | 3,880 |
| homodeoxyharringtonine | NA* | NA | NA |
| isoharringtonine | 230 | 770 | 1,000 |
| harringtonine | 170 | 140 | 310 |
| homoharringtonine | 330 | 750 | 1,080 |

*Not analyzed.

Example 8 (6 months)

| Alkaloid | In callus (μg./kg.) | In medium (μg./kg.) | Total (μg./kg.) |
|---|---|---|---|
| cephalotaxine | 780 | 5,750 | 6,530 |
| deoxyharringtonine | — | 990 | 990 |
| homodeoxyharringtonine | — | 80 | 80 |
| isoharringtonine | 220 | 1,920 | 2,140 |
| harringtonine | trace | 430 | 430 |
| homoharringtonine | 10 | 1,070 | 1,080 |

It is understood that the foregoing detailed description is given merely by way of illustration and that modification and variations may be made therein without departing from the spirit and scope of the invention.

We claim:

1. A method of producing alkaloid compounds selected from the group consisting of cephalotaxine, harringtonine, isoharringtonine, homoharringtonine, deoxyharringtonine and homodeoxyharringtonine from *Cephalotaxus harringtonia* callus comprising the steps of:
   a. providing living tissue of *Cephalotaxus harringtonia*;
   b. providing a nutrient culture medium suitable for callus formation from said tissue;
   c. culturing said tissue on said medium to produce callus from said tissue whereby said callus actively secretes said alkaloid compounds into said medium; and
   d. recovering said actively secreted alkaloid compounds from said medium.

2. The method as described in claim 1 wherein said living tissue in step (a) is leaf tissue.

3. The method as described in claim 1 wherein said culture medium is an aqueous solution and is absorbed into a bridge of absorbent material at least partially immersed in said solution.

4. The method as described in claim 1 wherein said actively secreted alkaloid compound recovered from said medium in step (d) is homodeoxyharringtonine.

* * * * *